United States Patent [19]

Stepniczka

[11] 3,965,197
[45] June 22, 1976

[54] PROCESS FOR THE COMPLETE BROMINATION OF NON-FUSED RING AROMATIC COMPOUNDS

[75] Inventor: Heinrich Stepniczka, Alma, Mich.

[73] Assignee: Michigan Chemical Corporation, Chicago, Ill.

[22] Filed: Jan. 17, 1972

[21] Appl. No.: 222,412

Related U.S. Application Data

[62] Division of Ser. No. 80,122, Oct. 12, 1970, abandoned.

[52] U.S. Cl............................ 260/623 H; 260/608; 260/609 R; 260/611 A; 260/612 R; 260/649 R; 260/650 R
[51] Int. Cl.$^2$................. C07C 39/36; C07C 43/00; C07C 149/32
[58] Field of Search ....... 260/608, 612, 620, 611 A, 260/649 R, 649 D, 650 R, 623 H, 650 R, 612 R, 607 R, 649, 609

[56] References Cited
UNITED STATES PATENTS 2,022,634   11/1935   Britton et al.................... 260/612 R
3,285,965   11/1966   Jenkner ............................ 260/612
3,752,856   8/1973    Nagy et al....................... 260/623 H Primary Examiner—James O. Thomas, Jr.
Assistant Examiner—W. B. Lone
Attorney, Agent, or Firm—Robert M. Phipps; Robert S. Frieman

[57] ABSTRACT

There is disclosed a process for the preparation of completely brominated derivatives of aromatic compounds comprising one or more phenyl groups which may contain substituents, side chains or be partially-brominated. The complete bromination is effected by utilizing liquid bromine as a reaction solvent whereby the starting aromatic material is reacted with an excess of bromine which contains a bromination catalyst and the mixture is refluxed for a sufficient time. Use of these brominated derivatives as fire retarding agents is nylon and polyester is also disclosed.

14 Claims, No Drawings

PROCESS FOR THE COMPLETE BROMINATION OF NON-FUSED RING AROMATIC COMPOUNDS

CROSS-REFERENCE TO RELATED APPLICATIONS

This application is a division, of patent application Ser. No. 80,122, filed Oct. 12, 1970, now abandoned.

The present invention relates to completely brominated derivatives of aromatic compounds and particularly to the process for the preparation of said derivatives, said process being characterized by utilizing liquid elementary bromine as a reaction solvent. Moreover, the invention is concerned with the utility of these brominated derivatives as fire-retarding agents in synthetic polymeric systems such as polyester and polyamide.

Aromatic hydrocarbons comprising one or more benzene rings have been partially brominated by various methods. In fact, introducing up to three bromine atoms per one aromatic molecule is usually accomplished with relative ease to the extent that a number of brominating agents can be used. Difficulties are encountered, however, when further bromination, beyond the tri-bromo level, is desired. Encountering such difficulties is not unexpected since it is known that substituted ring positions tend to reduce the activity level of adjacent, but unsubstituted, positions. Thus more drastic and stringent reaction conditions are necessary to effect further introduction of bromine into the ring. For example, in the prior art, to prepare hexabromobenzene from benzene, mono-, or dibromobenzene the bromination is conducted in concentrated sulfuric acid containing 29% free sulfur trioxide. The reaction time is lengthy, usually between 9 to 16 hours and is generally carried at elevated temperatures, i.e. about 150°C. Reaction conditions of comparable harshness are used to prepare other highly brominated aromatic compounds such as tetrabromoaniline, octabromobiphenyl and decabromobiphenyl, see U.S. Pat. No. 3,232,959.

The bromination of aromatic compounds utilizing bromine or other brominating agents is conducted generally in the presence of solvents which provide convenient reaction media insofar as solubilities, ease of handling and reaction with some formed by-products as means of the elimination thereof. A number of suitable solvents has been proposed including halogenated aliphatic compounds, organic and inorganic acids. For example, carbon tetrachloride, chloroform, alkylene dihalides containing 2 to 4 carbon atoms such as ethylene-, propylene-, butylene-, isobutylene dichlorides or dibromides, acetic acid and concentrated sulfuric acid have been utilized. Oleum containing some free sulfur trioxide proved to be a very good solvent. Evidently the aromatic compound reacts first with the sulfuric acid to form the corresponding monosulfonic acid and water. When bromine is introduced into the solvent, it will react with the monosulfonic acid to form the bromo-derivative and hydrobromic acid. But two undesirable by-products are constantly produced, i.e. water and HBr. Because the solvent medium contains free $SO_3$ which is a strong oxidizer the HBr is reoxidized to bromine with the additional formation of water. At this rate it can be seen that the concentration of the sulfuric acid is continuously decreased which in turn will affect adversely the sulfonation reaction which requires a strong acidic medium. It is for this reason that sufficient amounts of sulfur trioxide are added to maintain the sulfuric acid concentration at the proper level.

In the oleum process, the reaction temperatures employed will often influence the sulfonation of aromatic compounds which already contain substituents. This influence is observed in the ring position of the introduced sulfo group. In this respect formation of m-sulfonic acids is undesirable and it is necessary, therefore, to control the reaction temperature in such a manner as to eliminate the formation of these by-products which are very difficult to brominate completely.

Use of solvents, other than oleum, in the preparation of brominated derivatives of aromatic compounds has been somewhat limited because of the bromination of the solvent itself. Unless the brominated solvent is in itself desirable the process becomes expensive. In the event the solvent cannot be brominated such as carbon tetrachloride or other perchloro compounds, problems relating to decomposition, solubility, recovery of solvent and separations of finished products are encountered.

In order to produce completely brominated derivatives of aromatic compounds in high yields processes different from the above were necessarily indicated.

According to the present invention a process has been devised whereby completely brominated derivatives of aromatic compounds are prepared from the action of bromine solvent on the corresponding aromatic compound, in the presence of a bromine-transfer catalyst. Thus bromine is used herein as a reactant-solvent. At this juncture mention should be made that the present invention is not concerned with aromatic compounds having fused or condensed rings such as naphthalene, anthracene and similarly related compounds. The invention, however, is concerned with aromatic compounds having one or more benzene ring, which may have substituents, such as benzene, toluene, phenol, xylene, biphenyl, biphenylether, biphenyl sulfide, and the like. Also it is to be understood that the starting material may be partially brominated such as brominated benzenes and biphenyls.

The particular advantages of the process of the present invention are the absence of a solvent other than bromine, the relatively low reaction temperatures, the high yields and the purity of the brominated products. The bromination is carried out in the presence of a bromination catalyst such as iron, aluminum, their halides, iodine and mixtures thereof. The quantity of the catalyst depends on the reactants used. For example it has been found that about 2.5 g of $AlBr_3$ per 1 mole of benzene was needed to effect the complete bromination to hexabromobenzene. Below about 2.5 g/mol, only mono- and dibromobenzene could be obtained. It appears that the amount of catalyst required depends greatly on the amount of water present, because of the hydrolysis of $AlBr_3$. Water, therefore, should be kept at minimum levels.

As to the hydrogen bromide produced during the reaction, it is easily removed in its gaseous state. As such the HBr may entrain some of the reactants, usually bromine which can be trapped and recycled to the reaction vessel.

Inasmuch as the present invention contemplates a process of general application, it should be borne in mind that minor modifications may be necessary depending on the starting material, equipment availability and desired product quality. The bromination reaction may generate a great deal of heat because of the exothermic nature of the reaction. Thus the time needed to complete the bromination of the aromatic compound may depend on the size of reaction vessel, the efficiency of the cooling system along with the stirring and mixing operation. Moreover the amount of catalyst used will also influence the reaction time.

The fact that bromine operates as a solvent as well as a reactant the amount thereof is expected to be in a good excess over stoichiometric requirements. It has been found that an excess of 100% of bromine is satisfactory in that little or no under-bromination results. Of course, if desired, greater excess can be used. After the reaction is complete the excess bromine can be easily separated from the finished product. It is believed that most, if not all completely brominated derivatives of aromatic compounds are insoluble in liquid bromine. The final mixture, therefore, can be filtered under slight pressure. Alternatively the bromine can be steam-stripped out of the reaction vessel with little loss. Air can also be used for that purpose. With steam, however, recovery of bromine was over 94%.

It is well known that to maintain a reasonable rate of reaction requires a higher temperature as each additional bromine is substituted. This is true in the oleum process which starts at ambient or lower temperatures and as the bromination proceeds heat is supplied until the reaction temperature reaches usually about 150°C. The process of the present invention starts similarly at ambient or lower temperatures at which stage the bromination is rapid and exothermic. As the reaction subsides, indicating that the hydrocarbon has at least been partially brominated, heat is supplied to the reaction vessel until the bromine starts to reflux. Refluxing is continued until slightly after the reaction is completed. Completion of the reaction is observed when the evolution of hydrogen bromide ceases. The additional refluxing is precautionary so that no underbromination occurs.

In order to illustrate some of the advantages of the instant invention the following examples are provided and in which the proportions are given in parts by weight unless specified otherwise.

EXAMPLE I

Preparation of Hexabromobenzene

To a 300 ml three-necked flask equipped with a reflux condenser, stirrer, a dropping funnel and a thermometer 425 g of liquid bromine was added. 0.5 g of $AlBr_3$ was also added to the mixture which was agitated to allow the catalyst to dissolve in the bromine completely. The bromine - $AlBr_3$ mixture was then cooled to about 15°C. and maintained at that temperature during the gradual addition of 15.6 g of benzene. The bromination reaction is quite rapid and care should be taken so that not much bromine and benzene are entrained with the evolving hydrogen bromide. Thus the size of the reaction vessel and the efficiency of the cooling and condenser system are important in this respect.

After the benzene was added, about one hour, the need for cooling the reaction vessel was no longer necessary. In fact the mixture was allowed to warm up slowly and afterwards heat was supplied to bring the bromine to reflux to about 60°C. The reflux was maintained for an hour. Here the amount of catalyst added and the stirring efficiency affect the length of the reflux period; more catalyst and efficient stirring reduces the time of reflux considerably. The excess bromine was removed by blowing superheated steam (about 140°C.) through the reaction vessel and collecting the bromine in an outside vessel. Within a few minutes only a thick slurry of hexabromobenzene remained which was filtered, washed with hot dilute hydrochloric acid, filtered and finally washed with hot water and dried at 75°C. The yield of the light tan crystalline product was 96.7% based on benzene. Determination of bromine and IR spectrum showed the product to be essentially hexabromobenzene, said product having a melting point of 329°–330°C.

EXAMPLE II

Preparation of Pentabromotoluene

To a similar apparatus as described in Example I 471 g of liquid bromine (151 mls) was added to the 300 ml flask. 2.0 g of $AlBr_3$ was also added and allowed to dissolve in the bromine. 0.2 moles of toluene (21.35 mls) was gradually added to the cooled flask (about 10°–15°C.) making sure that sublimation or rapid evolution of HBr was not such as to entrain too much of the reactants. The addition of the toluene was carried out over one hour after which the flask was allowed to warm up and later it was heated until the bromine commenced to reflux (58°C.) at which temperature the reaction was continued until no further evolution of HBr was observed (occasionally the temperature was slightly increased to maintain continuous reflux).

The solid product was filtered after removing the bulk of bromine. After washing with hot dlute HCl and hot water the product was dried at 105°C. Weight obtained was 93.5 g of slightly tan crystals which on analytical examination showed to be pentabromotoluene m.p. 286°–287°C.

EXAMPLE III

Preparation of Tetrabromo-p-xylene

To a similar apparatus as described in Example I, 220 g of $Br_2$ was added and 1.0 g of $AlBr_3$ was dissolved therein. To the cold mixture 10.62 g of p-xylene was added very slowly over about one hour. The mixture of bromine, catalyst and xylene was then refluxed at about 60°C. for about 2–3 hours until no HBr was detected. The solid product was filtered, washed in the same manner as described under Examples I and II. The slightly yellow crystals weighed 39.6 g and analytical tests showed them to be tetrabromo-p-xylene having a melting point of 247°–249°C. and a yield of about 94%.

EXAMPLE IV

Preparation of Pentabromophenol a. From phenol

In this preparation 475 g of bromine in which 2 g of $AlBr_3$ was dissolved. 18.8 g of phenol was slowly added and later the mixture was heated to about 60°C. at which temperature the bromine reflux was maintained for a period of 2 hours. HBr was observed to evolve very rapidly in the early part of the reaction.

After removal of excess bromine the crystalline product was filtered and washed as usual with hot dilute HCl and water respectively. The dried product had a melting point of 225°–227°C. and based on analytical data it was shown that the brominated derivative is pentabromophenol.

b. From anisole

To a similar apparatus as described in Example I 471 g of bromine and 2 g of AlBr$_3$ were added and allowed to dissolve. 21.6 g of anisole was added slowly to the bromine-catalyst mixture. The reaction was carried out in the same manner as described above. However instead of obtaining brominated anisole, analytical data showed the product to be pentabromphenol. It appears that the bromination in this reaction cleaved the molecule at the oxygen bridge forming the phenolic product.

EXAMPLE V

Preparation of Decabromobiphenyl

To a 500 ml three-neck flask equipped similarly to those used in prior Examples, was added about 80 ml of bromine (250 g). The flask was cooled to about 10°C. 30.84 g of biphenyl was added in very small amounts to the bromine. To another portion of bromine (about 150 ml; total of two portions was 725 g) was added 10 g of AlBr$_3$ which was allowed to dissolve therein. After all the biphenyl was added to the first portion then the second portion was added. It should be understood that the addition of the bromine was effected via the dropping funnel, since the biphenyl is solid. In all the experiments the apparatus is equipped with a stirrer and/or suitable means. The mixture was then allowed to warm up and later heated to 60°C. at which temperature the refluxing of bromine was observed. Bromine reflux was continued for about 4 hours and the solid tan colored crystals were collected, washed with hot dilute HCl and water, respectively. Analysis showed that the product contained 84.77% bromine and had a melting point of 385°–389°C. with a yield of 95%.

EXAMPLE VI

Preparation of Decabromobiphenyl ether

To an apparatus similar to the one used in Example V 34.05 g of biphenylether and a total of 782 g of bromine (added in two portions, the second containing 5 g of AlBr$_3$) were reacted in the same manner described in Example V above. The reaction is quite rapid and slow addition was necessary. The mixture was allowed to warm after the evolution of HBr slowed down. Heat was applied to the mixture until the bromine started to reflux. The solid-liquid bromine mixture was treated as described in the prior Examples to separate the brominated derivative. The final product obtained was yellowish in color. Analysis showed the product to be decabromobiphenylether containing bromine to the extent of 83.42% and oxygen = 1.79%. The yield was also over 90% of theoretical based on biphenylether.

EXAMPLE VII

Preparation of Decabromobiphenylsulfide

In an identical apparatus as used in Example VI 37.6 g of biphenylsulfide was placed in the 300 ml three-neck flask. 780 g of bromine in two portions were added; the second portion containing 5 g of AlBr$_3$. Prior to the addition of the second portion the mixture was kept cool at about 10°C. Very strong evolution of HBr was observed. The second portion was added after the reaction subsided. The entire mixture was then refluxed for a period of about 4 hours. Additional 150 g of bromine was added. The final brominated product was filtered off after the evolution of HBr ceased. Bromine was removed by steam as described in Example I. The product was washed with hot dilute HCl and water several times and was later dried at 60°C. The grayish color crystals weighed 198.3 g and were analyzed to be decabromobiphenylsulfide; bromine content was 83.23%, S = 2.65% O = negligible.

At this juncture mention should be made that other catalysts have been used in experiments comparable to those described in Examples I-VII. These catalysts were aluminum metal, aluminum chloride, iron metal, ferric chloride and iodine. Of course some adjustments were necessary such as increasing the amount of liquid bromine and/or insuring that the final product was free of the chlorides or iodides. It is also important to relate that the brominating process of the present invention is not directed to aromatic compounds having fused or condensed rings such as naphthalene, anthracene and the like.

The effect of halogens and/or halogen-containing compounds on retarding and extinguishing fires is well known. Many chlorinated and brominated organic compounds have been incorporated or added to many polymeric systems for fire retardation purposes. Selection of the particular halogenated compound (s) for use with certain polymeric systems is not easy but, indeed, the result of considerable research efforts. In the case of fire retarding agents of the additive type it is significant that the agent satisfies the requirements of being (a) compatible with the polymeric system (b) not migratory, and (c) of comparable thermal stability. To be compatible specifies that the fire retarding agent can be blended with the polymer without affecting its mechanical and chemical properties. Further, it should not be of such a nature as to cause the migration of its particles toward the surface of the polymer. Finally it is important that the fire retarding agent has a decomposition range similar to the polymer itself. For the last mentioned property, it should be noted that should the fire retarding agent decompose or break-down prior to the decomposition of the polymeric system then it will afford little, if any, fire retardation. In the same manner should the fire retarding agent commence to decompose after the break-down of the polymer, the time lag or delay may be such that the fire retarding agent will be of no value. Thus it is an ideal property to provide a fire retarding agent possessing identical decomposition properties as the polymer. In practice one usually finds that the decompositions of the two materials, i.e., the polymer and the fire retarding agent are closely related.

In view of the above it becomes apparent that the selection of a suitable fire retarding agent is not arbitrary, especially in the case of high melting polymers or those requiring hot temperature processes for their manufacture such as polyamide (nylon) or linear polyester, respectively.

Completely brominated derivatives of biphenyl compounds such as decabromobiphenyl, decabromobiphenyl ether and decabromobiphenyl sulfide have been found to possess excellent fire retarding characteristics. Tests of these compounds on polyamide and polyester have given excellent results as will be shown hereinafter. The fire retardancy of the polymers was determined by the Oxygen Index Method which is now recognized for use on plastic materials by the American Society for Testing and Materials (ASTM) of 1916 Race Street, Philadelphia, Penn. 19103, and said test has been given the designation D 2863-70 (See Annual Book of ASTM Standards — effective May 8, 1970).

The Oxygen Index, also known as the Limiting Oxygen Index (L.O.I.) is defined as the minimum volume-fraction of oxygen in an atmosphere of oxygen and nitrogen, which is needed to sustain the candle-like burning of a polymeric specimen. For further explanation and theoretical discussion, reference is made to a paper by J. DiPietro and H. Stepniczka presented at the Society of Plastic Engineers Conference, New York, N.Y., May 6, 1970, and published in Plastic Engineer Society, Inc., Volume XVI, pp. 463–468.

The Oxygen Index (O.I.) for air is 0.209. The higher the value the less likely it is for the polymeric system to burn or sustain buring. In fact it is known that polymer systems having O.I. values about 0.27–0.28 can be considered self-extinguishing in nature.

In Table I below there are provided data on the fire retardancy of both nylon and linear polyester, said data being expressed in terms of the Oxygen Index. Synergists such as antimony trioxide can be added to enhance the fire retardancy.

TABLE I

| Polymer | Fire Retarding Agent and Percent | | $Sb_2O_3$ % | Oxygen Index |
|---|---|---|---|---|
| Nylon | 0 | | 0 | 0.202 |
| Nylon | DBBPS[a], | 6.1 | 0 | 0.214 |
| Nylon | DBBPS[a], | 12.2 | 0 | 0.229 |
| Nylon | DBBPS[a], | 18.3 | 0 | 0.239 |
| Nylon | DBBPS[a], | 24.4 | 0 | 0.250 |
| Nylon | DBBPS[a], | 6.1 | 1.2 | 0.221 |
| Nylon | DBBPS[a], | 12.2 | 2.4 | 0.251 |
| Nylon | DBBPS[a], | 18.3 | 3.6 | 0.280 |
| Nylon | DBBPS[a], | 24.4 | 4.8 | 0.303 |
| Polyester (Dacron)* | 0 | | 0 | 0.212 |
| Polyester (Dacron)* | DBBP[b], | 5.0 | 0 | 0.259 |
| Polyester (Dacron)* | DBBP[b], | 10.0 | 0 | 0.293 |
| Polyester (Dacron)* | DBBP[b], | 20.0 | 0 | 0.372 |
| Polyester (Dacron)* | DBBP[b], | 10.0 | 2.0 | 0.385 |

*Trade-Mark of E. I. DuPont De Nemours & Co., Inc.
[a]Decabromobiphenylsulfide
[b]Decabromobiphenyl It is to be understood that the foregoing detailed description is merely given by way of illustration and that other variations may be made therein without departing from the scope of the invention as defined by the following claims.

What is claimed is:

1. A process for the complete bromination of aromatic compounds on the ring portion thereof, said aromatic compounds having one or more benzene rings and are selected from the group consisting of benzene, toluene, phenol xylene, biphenyl, biphenylether and biphenyl sulfide, comprising the steps of:
    a. reacting the aromatic compound with a large excess of liquid bromine in the presence of a bromination catalyst selected from the group consisting of iron, aluminum, iodine, iron halide, and aluminum halide, at from about 10°C. to ambient temperatures to form a reaction mixture with the evolution of gaseous hydrogen bromide, said bromine excess being at least 100 percent of the stoichiometric amount of bromine required for the complete bromination;
    b. thereafter refluxing said reaction mixture;
    c. maintaining said reflux condition for a time sufficient whereby hydrogen bromide ceases to form; and
    d. separating the completely brominated aromatic reaction product from the reaction mixture.

2. A process for the preparation of completely brominated derivatives of aromatic compounds according to claim 1 wherein said bromination catalyst is selected from aluminum halides, iron halides and iodine.

3. A process according to claim 1 wherein the reaction mixture formed in step a. is maintained about 10 degrees Centigrade to control the initial bromination reaction.

4. A process for the preparation of completely brominated derivatives of aromatic compounds according to claim 1 which is further characterized by having the reaction mixture stirred throughout the bromination reaction.

5. A process for the preparation of completely brominated derivatives of aromatic compounds according to claim 1 wherein the derivative of step (d) is treated with super-heated steam to remove any occluded bromine.

6. A process according to claim 1 wherein the completely brominated aromatic reaction product is selected from the group consisting of pentabromophenol, pentabromotoluene and tetrabromoxylene.

7. A process for the preparation of completely brominated derivatives of aromatic compounds according to claim 2 wherein said catalyst is selected from aluminum and iron chlorides.

8. A process according to claim 1 wherein the said completely brominated aromatic derivative is washed and dried.

9. A process for completely brominating an aromatic compound selected from biphenyl, biphenyl ether and biphenyl sulfide to produce the corresponding decabrominated derivative, comprising the steps of:
    a. reacting the aromatic compound with liquid bromine in the presence of a bromination catalyst selected from the group consisting of iron, aluminum, iodine, iron halide and aluminum halide at from about 10°C. to ambient temperature to form a reaction mixture with the evolution of gaseous hydrogen bromide, said liquid bromine being present in said mixture in an amount in excess of the stoichiometric amount of bromine by an amount at least 100 percent of the stoichiometric amount required for the complete bromination;
    b. thereafter refluxing said reaction mixture;
    c. maintaining said reflux condition for a sufficient time whereby hydrogen bromide ceases to form; and
    d. separating the formed decabrominated derivative from the reaction mixture.

10. A process according to claim 9 wherein the reaction mixture formed in step a. is maintained at about 10 degrees Centigrade to control the initial bromination.

11. A process for completely brominating an aromatic compound selected from biphenyl, biphenyl ether and biphenyl sulfide according to claim 9 wherein the decabrominated derivative is treated with super-heated steam to remove any occluded elemental bromine.

12. A process for completely brominating an aromatic compound selected from biphenyl, biphenyl ether and biphenyl sulfide according to claim 9 wherein the reaction mixture is kept stirred throughout the bromination reaction.

13. A process according to claim 9 wherein said bromination catalyst is selected from aluminum halides, iron halides and iodine.

14. A process according to claim 9 wherein said decabrominated derivative is washed and dried.

* * * * *